United States Patent [19]

Matthes et al.

[11] Patent Number: 5,496,935
[45] Date of Patent: Mar. 5, 1996

[54] 2',3'-DIDEOXYNUCLEOSIDE PYRIMIDINE COMPOUNDS AND CARBOCYCLIC ANALOGS

[75] Inventors: Eckart Matthes; Martin von Janta-Lipinski; Dieter Scholz; Klaus Gaertner; Juergen Schildt; Christine Lehmann; Peter Langen; Hans A. Rosenthal, all of Berlin, Germany

[73] Assignee: Max-Delbrück-Centrum, Berlin, Germany

[21] Appl. No.: 227,587

[22] Filed: Apr. 14, 1994

Related U.S. Application Data

[63] Continuation of Ser. No. 48,386, Apr. 16, 1993, abandoned, which is a continuation of Ser. No. 933,593, Aug. 20, 1992, abandoned, which is a continuation of Ser. No. 395,393, Aug. 16, 1989, abandoned.

[51] Int. Cl.$^6$ .......................... C07H 19/06; C07H 15/20
[52] U.S. Cl. .................. 536/28.2; 536/28.1; 536/28.4; 536/28.5; 536/28.51; 536/28.52; 536/28.53; 536/28.54; 544/242
[58] Field of Search .................. 514/49, 50, 51, 514/52, 269, 274; 536/28.1, 28.2, 28.4, 28.5, 28.51, 28.52, 28.53, 28.54; 544/269, 274, 242

[56] References Cited

U.S. PATENT DOCUMENTS

| | | | |
|---|---|---|---|
| 3,817,982 | 6/1974 | Verheyden et al. | 536/27.14 |
| 4,177,348 | 12/1979 | Shealy et al. | 544/317 |
| 4,719,214 | 1/1988 | Shealy et al. | 514/274 |
| 4,880,782 | 11/1989 | Eckstein et al. | 514/45 |
| 4,963,662 | 10/1990 | Matthes et al. | 514/51 |
| 5,153,180 | 10/1992 | Matthes et al. | 514/50 |

FOREIGN PATENT DOCUMENTS 0355031  8/1989  European Pat. Off. ............ 536/28.2

OTHER PUBLICATIONS

Yarchoan et al., New England Journal of Medicine, vol. 316, pp. 557–564, (1987).

*Primary Examiner*—Douglas W. Robinson
*Assistant Examiner*—James O. Wilson
*Attorney, Agent, or Firm*—Schweitzer Cornman & Gross

[57] ABSTRACT

2',3'-dideoxynucleoside pyrimidine compounds and 2-thiothymidine carbocyclic derivatives with antiviral activity are disclosed. These compounds are expected to exhibit antiviral activity recognized for 2',3'-dideoxynucleoside compounds and analogs thereof.

1 Claim, No Drawings

2',3'-DIDEOXYNUCLEOSIDE PYRIMIDINE COMPOUNDS AND CARBOCYCLIC ANALOGS

This is a continuing application of U.S. Ser. No. 08/048,386, filed on Apr. 16, 1993 now abandoned, which is a continuing application of U.S. Ser. No. 07/933,593, filed on Aug. 20, 1992 now abandoned, which is a continuing application of U.S. Ser. No. 07/395,393, filed on Aug. 16, 1989 now abandoned.

FIELD OF THE INVENTION

The invention relates to substituted pyrimidine nucleosides, which are effective against infections caused in animal or man by viruses or retroviruses, especially HIV infections (AIDS) in man, and their use in the form of appropriate compositions.

BACKGROUND OF THE INVENTION

AIDS is an infectious disease, which has been known for a few years, is caused by the HIV (HTLV III/LAV, human T lymphotropic virus type III/lymphadenopathy-associated virus), and it leads to death. The destruction of the T helper cells by the AIDS virus must be regarded as causative of the disease. Serious opportunistic infections, such as Kaposi's sarcoma and the so-called AIDS encephalopathy occur as a consequence of the resulting lowered resistance. There has so far not been an effective and tolerated antiviral therapy. One point of attack for such a therapy may be the virus-coded reverse transcriptase, an enzyme, the suppression of which can prevent the further intracellular reproduction of the virus and thus repress its spread in the body. The first clinically tested inhibitors of the HIV revertase, such as Suranim (GERMANIN®) have not yet attained the necessary tolerance and the hoped-for effectiveness. Only the 3'-azidothymidine ($N_3$TdR) (see German Federal Republic patent No. 3,500,606) has unambiguous life prolonging effects in AIDS patients with *Pneumocystitis carinii* pneumonia. These effects are accompanied by improvements in clinical and neurological findings, as well as by occasional restoration of certain immunological functions (Fischl et al., The New England J. of Medicine 317, 185 (1987)). As against this, the toxic side effects on the bone marrow of the 3'-azidothymidine make blood transfusions necessary in about 50% of the patients and points to the need for more selective inhibitors of the HIV reverse transcriptase; at the same time, their effectiveness should also be increased.

DESCRIPTION OF THE INVENTION

It is an object of the invention to provide novel pyrimidine nucleosides which can be used for the therapeutic treatment of AIDS or of infections caused by viruses or retroviruses and which, in comparison to known drugs, have a lesser toxicity and fewer side effects. The preparation of these nucleosides and their use in composition are additional objects of the invention.

The novel pyrimidine nucleosides have the formulae (I), (II), (III), or (IV)

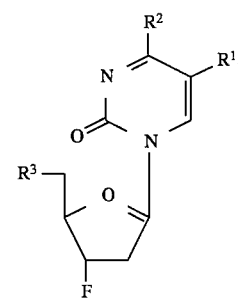

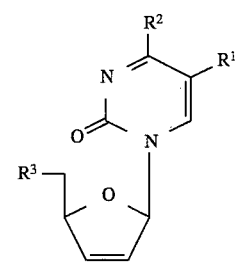

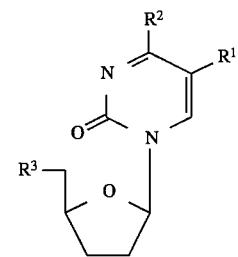

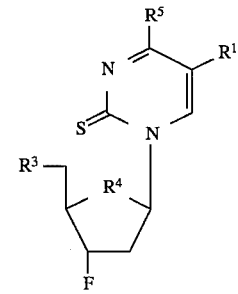

wherein
- $R^1$ is hydrogen, halogen, azido, $C_{1-5}$ alkyl, or $C_{2-5}$ alkenyl residue;
- $R^2$ is hydrogen, thio, thiomethyl, hydroxylamino, or $C_1$ alkyl containing amino, residue;
- $R^3$ is hydroxyl, O-acetyl, O-palmitoyl, O-alkoxycarbonyl, mono-, di- or triphosphoric acid, -alkali phosphate, -ammonium phosphate or -alkylammonium phosphate residue;
- $R^4$ is C or O; and
- $R^5$ is $R^2$, or O.

These nucleosides are effective against infections caused by viruses and retroviruses.

The reaction schemes for the preparation of the pyrimidine nucleosides of formulae (I), (II), (III) and (IV) are known per se in the art. For example, the 4-thio compounds are obtained by reacting the corresponding (1H, 3H)-pyrimidine-2-,4-dione compounds with phosphorous pentasulfide in pyridine according to the method disclosed by J. J. Fox et al., J. Amer. Chem. Soc. 81, 178–187 (1959). The 4-hydroxylamino and 4-alkylamino compounds are obtained by reacting the corresponding thio compounds with appropriate alkylamine or hydroxylamine by the method disclosed by J. J. Fox et al, cited above. The (1H)-pyrimidine-2-one compounds are prepared by reacting the appropriate 2,4-dione compounds with hydrazine to form the corresponding 4-hydrazine compounds and then oxidizing them with silver oxide. The -2',3'-dideoxy-2',3'-didehydro compounds are obtained from the corresponding 3',5'-di-O-mesyl compounds by splitting the mesyl group according to the method of J. P. Horwitz et al, J. Org. Chem. 31, 205–211 (1966). The -2',3'-dideoxynucleosides are obtained by hydrogenating the corresponding unsaturated compounds with hydrogen and 10% palladium/charcoal as the catalyst according to the method of J. P. Horwitz et al., cited above.

The preferred nucleosides of the invention are:
1-(2,3-dideoxy-3-fluoro-β-D-ribofuranosyl)-5-methyl-(1H)-pyrimidine-2-one;
1-(2,3-dideoxy-3-fluoro-β-D-ribofuranosyl)-4-thiothymine;
1-(2,3-dideoxy-3-fluoro-β-D-ribofuranosyl)-4-methylmercapto-5-methyl-(1H)-pyrimidine-2-one;
1-(2,3-dideoxy-3-fluoro-β-D-ribofuranosyl)-4-hydroxylamino-5-methyl-(1H)-pyrimidine-2-one;
5-chloro-1-(2,3-dideoxy-3-fluoro-β-D-ribofuranosyl)-4-thiouracil;
1-(2,3-dideoxy-3-fluoro-β-D-ribofuranosyl)-(1H)-pyrimidine-2-one;
1-(2,3-dideoxy-3-fluoro-β-D-ribofuranosyl)-4-thiouracil;
1-(2,3-dideoxy-3-fluoro-β-D-ribofuranosyl)-4-hydroxylamino-(1H)-pyrimidine-2-one;
1-(2,3-dideoxy-β-D-glycero-pent-2-enofuranosyl)-4-thiothymine;
1-(2,3-dideoxy-bβD-glycero-pent-2-enofuranosyl)-5-methyl-(1H)-pyrimidine-2-one;
1-(2,3-dideoxy-β-D-glycero-pent-2-enofuranosyl)-4-hydroxylamino-(1H)-pyrimidine-2-one;
1-(2,3-dideoxy-β-D-glycero-pent-2-enofuranosyl)-4-dimethylamino-(1H)-pyrimidine-2-one;
1-(2,3-dideoxy-3-fluoro-β-D-ribofuranosyl)-5-methyl-pyrimidine-2-one;
1-(2,3-dideoxy-3-fluoro-β-D-ribofuranosyl)-pyrimidine-2-one;
2',3'-dideoxy-2',3'-didehydro-4-thiothymidine;
1-(2,3-dideoxy-3-fluoro-β-D-ribofuranosyl)-2-thiothymine;
1-(5-0-acetyl-2,3-dideoxy-3-fluoro-β-D-ribofuranosyl)-2-thiothymine;
1-(5-0-acetyl-2,3-dideoxy-3-fluoro-β-D-ribofuranosyl)-2,4-dithiothymine;
1-(2,3-dideoxy-3-fluoro-β-D-ribofuranosyl)-2,4-dithiothymine;
1-(2,3-dideoxy-3-fluoro-β-D-ribofuranosyl)-5-ethyl-4-thiouracil;
(±)-1-[1β,4β)-4-(trityloxymethyl)-cyclopent-2-en-1-yl]-2-thiothymine;
(±)-1-[1β,3,4β)-3-fluoro-4-(trityloxymethyl)-cyclopentyl]-2-thiothymine;
(±)-1-[1β,4β)-4-(hydroxymethyl)-cyclopent-2-en-1-yl]-2-thiothymine;
(±)-1-[1β,3α,4β)-3-fluoro-4-(hydroxymethyl)-cyclopentyl]-2-thiothymine;
3'-deoxy-3'-fluoro-4-thiothymidine (I);
3'-deoxy-4-thiothymidine (III);
1-(5-O-acetyl-2,3-dideoxy-3-fluoro-β-D-ribofuranosyl)-4-thiothymine;
1-(5-O-acetyl-2,3-dideoxy-3-fluoro-β-D-glycero-ribofuranosyl)-4-hydroxylamino-(1 H)-pyrimidine-2-one;
1-(2,3-dideoxy-3-fluoro-β-D-glycero-ribofuranosyl)-4-hydroxylamino-(1H-)pyrimidine-2-one;
1-(5-O-acetyl-2,3-dideoxy-3-fluoro-β-D-ribofuranosyl)-4-hydroxylamino-5-methyl-(1 H)-pyrimidine-2-one;
1-(5-O-acetyl-2,3-dideoxy-β-D-glycero-pent-2-enofuranosyl)-4-thiothymine;
1-(2,3-dideoxy-3-fluoro-β-D-ribofuranosyl)-4-thiothymine-5'-triphosphate.

The compositions of the present invention contain at least one compound of the formulae (I) and/or (II) and/or (III) as active ingredient, together with at least one compatible carrier and, if necessary, other therapeutic materials. The compositions are suitably prepared as a standard dose, suitably containing more than one type of the three types of active ingredients and/or other actives. Each carrier must be compatible, and combinable with the other components of the composition and not harmful to the patient.

The compositions of the invention include those, which are suitable for oral, rectal, nasal, topical, vaginal or parenteral (including subcutaneous, intramuscular, intravenous and intradermal) administration.

The compositions for oral administration are prepared in the form of coated or uncoated tablets, capsules, or as a powder or granulate so that they contain an effective amount of the active ingredient or ingredients. Likewise, they can be prepared as a solution or as a suspension. If necessary, materials that impart a desirable taste or other conventional materials are added to the composition. Compositions for rectal administration are prepared as suppositories with a suitable base. Compositions for a vaginal administration are prepared as pessaries, tampons, creams, gels, pastes, foams or spray products.

The composition for parenteral administration can be provided as a standard dose of the active ingredient or as a multiple dose. For this purpose, they can be stored in ampoules, vials or in a freeze-dried state. Directly prepared injection solutions and suspensions can also be obtained from sterile powders, granulates and tablets. This is accomplished, for example, by dissolving the composition in physiological salt solution, glucose or other media suitable for i.v. injection or infusion.

The following compounds proved to be particularly effective and are most preferred. Their respective formula types are each indicated after the naming below of each compound.
1-(2,3-dideoxy-3-fluoro-β-D-ribofuranosyl)-5-methyl-(1H)-pyrimidine-2-one (I);
3'-deoxy-3'-fluoro-4-thiothymidine (I);
1-(2,3-dideoxy-3-fluoro-β-D-ribofuranosyl)-4-methylmercapto-5-methyl-(1H)-pyrimidine-2-one (I);
5-chloro-1-(2,3-dideoxy-3-fluoro-β-D-ribofuranosyl)-4-thiouracil (I);
1-(2,3-dideoxy-3-fluoro-β-D-ribofuranosyl)-(1H)-pyrimidine-2-one (I);
1-(2,3-dideoxy-3-fluoro-β-D-ribofuranosyl)-4-thiouracil (I);
1-(2,3-dideoxy-3-fluoro-β-D-glycero-pent-2-enofuranosyl)-4-dimethylamino-(1H)-pyrimidine-2 -one (II);
1-(2,3-dideoxy-3-fluoro-β-D-glycero-pent-2-enofuranosyl)-4-hydroxylamino-(1H)-pyrimidine-2 -one (II);
3'-deoxy-4-thiothymidine (III);
2',3'-dideoxy-2'-3'-didehydro-4-thiothymidine(I); and
1-(2,3-dideoxy-3-fluoro-β-D-ribofuranosyl)-5-methyl-pyrimidine-2-one(I).

The effectiveness of some of the novel compounds is shown below:
1. Selective inhibition of the HIV-associated reverse transcriptase (HIV-RT) by 3'-fluoro-4-thiothymidine-triphosphate For these investigations, the effect of the compound on the activity of HIV-RT as well as on the cellular DNA polymerase was determined using the methods described by Matthes et al., in Biochem. Biophys. Res. Commun. 148, 78 (1987). Different concentrations of 3'-fluoro-4-thiothymidine triphosphate were added to the enzyme preparations. The concentrations of 3'-fluoro-4-thiothymidine triphosphate, which inhibit the polymerases investigated to the extent of 50% ($ID_{50}$), were determined from the inhibition curves obtained. An $ID_{50}$ of 0.3 micromoles/L was determined for the HIV-RT, of 140 micromoles/L for the DNA polymerase, the enzyme mainly responsible for cellular replication, and of 7 micromoles/L for DNA polymerase β, the cellular DNA repair enzyme. Accordingly 3'-fluoro-4-thiothymidine triphosphate inhibits the HIV-RT 700 times more effectively than the cellular DNA polymerase and thus has a largely selective effect on the HIV replication.

2. Inhibition of the cytopathic effect of HIV on T lymphocyte cells

Under in vitro conditions, an infection of T lymphocytes with HIV leads to the death of the cells within a few days. The MT-4 cells, described by Harada et al. in Science 229, 563 (1985), were used in a test system (Matthes et al., Biochem. Biophys., Res. Commun. 153, 825 (1988)), to test to what extent the inventive nucleosides can nullify the cytocidal effect of HIV-1 (HTLV IIIa) on this T cell line. The concentrations, which lead to a 50% protection of the MT-4 cells, are given in the Table. In addition, the antiproliferative effectiveness of the nucleosides investigated is listed and, moreover, as the concentration which decreases the proliferation of the MT-4 cells by 50% ($CD_{50}$).

3. In vitro cytotoxicity of 3'-fluoro-4-thiothymidine to cell cultures

The results with MT-4 cells have shown that 3'-fluoro-4-thiothymidine has hardly any effect on the cell proliferation of this T cell line. A series of further human cell lines was included in the investigation of the antiproliferative effect of 3'-fluoro-4-thiothymidine and the following $CD_{50}$ were found:

| | |
|---|---|
| 1. REH, acute lymphatic leukemia = | 500 micromoles/L |
| 2. HELFI, human embryonic lung fibroblasts = | 700 micromoles/L |
| 3. H-8, immortalized T cell line => | 800 micromoles/L |
| 4. Molt-4, immortalized T cell line => | 1000 micromoles/L |

Moreover, 3'-fluoro-4-thiothymidine, in concentrations up to 100 micromoles/L, has no growth-inhibiting effect whatsoever on the colony-forming cells of the bone marrow of the mouse (GM-CFU).

In summarizing, 3'-fluoro-4-thiothymidine can therefore be characterized as an effective inhibitor of HIV replication, with very slight cytotoxicity.

TABLE

Comparison of the antiviral and antiproliferative effectiveness of nucleoside analogies using MT-4 cells

| nucleoside investigated | 50% antiviral dose ($ED_{50}$; micromoles/L) | 50% cytotoxic dose ($CD_{50}$; micromoles/L) |
|---|---|---|
| 1-(2,3-dideoxy-3-fluoro-β-D-ribofuranosyl)-4-thiothymine | 1.8 | 480 |
| 1-(2,3-dideoxy-3-fluoro-β-D-ribofuranosyl)-4-thiouracil | 15 | 150 |
| 1-(2,3-dideoxy-3-fluoro-β-D-ribofuranosyl)-4-methylmercapto-5-methylpyrimidine-2-one | >1000 | >1000 |
| 1-(2,3-dideoxy-3-fluoro-β-D-ribofuranosyl)-4-methylmercapto-pyrimidine-2-one | 12 | 50 |
| 1-(2,3-dideoxy-3-fluoro-β-D-ribofuranosyl)-4-hydroxylamino-5-methylpyrimidine-2-one | 100 | 300 |
| 1-(2,3-dideoxy-3-fluoro-β-D-ribofuranosyl)-4-hydroxylamino-pyrimidine-2-one | 100 | 100 |
| 1-(2,3-dideoxy-3-fluoro-β-D-ribofuranosyl)-5-methyl-pyrimidine-2-one | 12 | >400 |
| 1-(2,3-dideoxy-3-fluoro-β-D-ribofuranosyl)-pyrimidine-2-one | 30 | >800 |
| 2',3'-dideoxy-2',3'-didehydro-4-thiothymidine | 0.85 | 350 |

The following examples illustrate the preparation of the novel compounds, it being understood that these examples are given by way of illustration and not by way of limitation.

EXAMPLE 1

1-(2,3-Dideoxy-3-fluoro-β-D-ribofuranosyl)-4-thiouracil 1-(2,3-Dideoxy-3-fluoro-β-D-ribofuranosyl)-uracil (1.3 mmoles) is dissolved in 45 mL of pyridine and treated with 1.1 mL of acetic anhydride. The reaction mixture is allowed to stand overnight at room temperature. The solution is concentrated, the residue dissolved in toluene and evaporated to dryness once more. The process is repeated several times. The residue, finally obtained, is dissolved in 80 mL of pyridine, mixed with 3.9 mmoles of phosphorus pentasulfide and refluxed for 6 hours. After this reaction time, a further 1.3 mmoles of phosphorus pentasulfide are added (J. J. Fox et al., J. Am. Chem. Soc. 1959, 81, 178; G. Kowollik et al., J. Prakt. Chem. 1973, 315, 895) and the mixture is refluxed for 6 hours. The reaction mixture is allowed to cool and the liquid portion is separated is separated from the remainder and evaporated to dryness under vacuum. The resulting residue is purified by column chromatography on a silicage sold by Merck, Darmstadt under the trade name Kieselgel 40, with chloroform as eluting agent. 1-(5-O-Acetyl-2,3-dideoxy-3-fluoro-β-D-ribofuranosyl)-4-thiouracil is isolated from the appropriate fractions and, after recrystallization from 90% ethanol, is obtained in a yield of 97 mg and has a melting point of 140°–140.5° C. This compound (15 mg, 0.06 mmoles) is dissolved in 2 mL of methanol and mixed at 0'C with 2 mL of ammonia-saturated methanol. After 24 hours, the solution is evaporated to dryness. The compound is obtained as a glass.

MS: m/z 246 ($C_9H_{11}N_2O_3FS$, M$^+$), 128 ($C_4H_4N_2OS$, base+H) 119 ($C_5H_8O_2F$, sugar group).

EXAMPLE 2

1-(5-O-Acetyl-2,3-dideoxy-3-fluoro-β-D-ribofuranosyl)-4-thiothymine

5'-O-Acetyl-3'-fluorothymidine (400 mg, 1.4 mmoles) are heated under reflux for 24 hours with 933 mg of phosphorus pentasulfide in 32 mL of pyridine. After the solvent is driven off, the residue is fractionated by column chromatography on Kieselgel 40 and yields the desired compound as a yellow oil.

MS: m/z 302 ($C_{12}H_{15}N_2O_4SF$, $M^+$), 161 ($C_7H_{10}O_3F$, sugar group), 142 ($C_5H_8N_2OS$, base).

EXAMPLE 3

1-(2,3-Dideoxy-3-fluoro-β-D-ribofuranosyl)-4-thio-thymine

The compound (18 mg, 0.07 mmoles), obtained in Example 2, is dissolved in 2 mL of methanol, which has been saturated at 0'C with ammonia, and allowed to stand for 24 hours at room temperature. When the solvent is removed, 1-(2,3-dideoxy-3-fluoro-β-D-ribofuranosyl)-4-thiothymine is obtained as a glassy residue.

MS: m/z 260 ($C_{10}H_{13}N_2O_3FS$, $M^+$), 142 ($C_5H_6N_2OS$, base+H), 119 ($C_5H_8O_2F$, sugar group).

EXAMPLE 4

1-(5-O-Acetyl-2,3-dideoxy-3-fluoro-β-D-glycero-ribofuranosyl)-4-hydroxylamino-(1H)-pyrimidine-2-one 1-(5-O-Acetyl-2,3-dideoxy-3-fluoro-β-D-ribofuranosyl)-4-thiouracil (70 mg, 0.24 mmoles) is dissolved in 5 mL of methanol, mixed with 1 mL of hydroxylamine in 12 mL of methanol and heated for 4 hours under reflux. Thin-layer chromatography of the reaction solution shows that the reaction of the starting material has gone to completion. The solvent is removed under vacuum and the residue is purified on a Kieselgel 40 column with chloroform (2% methanol) as eluant. The desired compound is obtained in a yield of 60 mg from the appropriate fractions and crystallized from 90% ethanol. The melting point is 192°–193° C.

MS: m/z 287 ($C_{11}H_{14}N_3O_5F$, $M^+$), 161 ($C_7H_{10}O_3F$, sugar group), 127 ($C_4H_5N_2O_3$, base+H).

EXAMPLE 5

1-(2,3-Dideoxy-3-fluoro-β-D-glycero-ribofuranosyl)-4-hydroxylamino-(1H)-pyrimidine-2-one The compound (50 mg), obtained in Example 4, is deacetylated in the usual manner with ammonia/methanol. The compound is isolated as a glassy residue.

MS: m/z 245 ($C_9H_{12}N_3O_4$, $M^+$), 127 ($C_4H_5N_2O_3$, base+H), 119 ($C_6H_8O_2F$, sugar group).

EXAMPLE 6

1-(2,3-Dideoxy-3-fluoro-β-D-ribofuranosyl)-4-methylmercapto-5-methyl-(1H)-pyrimidine-2-one A solution of 70 mg (0.23 mmoles) of 1-5-O-acetyl-2,3-dideoxy-3-fluoro-β-D-ribofuranosyl)-4-thiothymine, 0.23 mL of 1N sodium hydroxide solution and 0.044 mL of methyl iodide in 4 mL of 50% methanol is allowed o stand at room temperature for 2 hours and then brought to a pH of 5 with acetic acid. After the solvent is driven off, 45 mg of 1-(2,3-dideoxy-3-fluoro-β -D-ribofuranosyl)-4-methylmercapto-5-methyl-(1H)-pyrimidine-2-one are obtained which, after recrystallization from ethanol, yields 32 mg of the pure product having a melting point of 192°–194° C.

MS: m/z 274 ($C_{11}H_{15}N_2O_3FS$, $M^+$), 156 ($C_8H_8N_2OS$, base+H), 119 ($C_5H_8O_2F$, sugar group).

EXAMPLE 7

1-(5-O-Acetyl-2,3-dideoxy-3-fluoro-β-D- ribofuranosyl)-4-hydroxylamino-5-methyl-(1 H)-pyrimidine-2-one 1-(5-O-Acetyl-2,3-dideoxy-3-fluoro-β-D-ribofuranosyl)-4-thiothymine (93 mg, 0.31 mmoles) is mixed with a solution of 1 mL of hydroxylamine in 15 mL of methanol and heated under reflux for 4 hours. The residue, remaining after removal of the solvent under vacuum, is purified by column chromatography on 75 g of Kieselgel 40 with chloroform as eluant. From the appropriate fractions, a total of 51 mg of a product is obtained which, after recrystallization from methanol, yields 35 mg of 1-(5-O-acetyl-2,3-dideoxy-3-fluoro-β -D-ribofuranosyl)-4-hydroxylamino-5-methyl-(1H)-pyrimidine-2-one with a melting point of 180°–181° C.

MS: m/z 301 ($C_{12}H_{16}N_3O_5F$, $M^+$), 161 ($C_7H_{10}O_3F$), sugar group), 141 ($C_5H_7N_3O_2$, base+H).

EXAMPLE 8

1-(2,3-Dideoxy-3-fluoro-β-D-ribofuranosyl)-4-hydroxylamino-5-methyl-(1H)-pyrimidine-2-one The compound (45 mg), prepared in Example 7, is treated in the usual manner with ammonia/methanol and, after crystallization, yields 27 mg of 1-(2,3-dideoxy-3-fluoro-β-D-ribofuranosyl)-4-hydroxylamino-5-methyl-(1 H)-pyrimidine-2-one.

MS: m/z 259 ($C_{10}H_{14}N_3O_4F$, $M^+$), 141 ($C_5H_7N_3O_2$, base+H), 119 ($C_5H_8O_2F$, sugar group).

EXAMPLE 9

1-(5-O-Acetyl-2,3-dideoxy-β-D-glycero-pent-2-enofuranosyl)-4-thiothymine

To a solution of 450 mg (2 mmoles) of 3'-deoxy-2'-thymidinene in 10 mL of pyridine, 1 mL of acetic anhydride is added. The reaction mixture is kept at room temperature for 10 hours. The solvent is driven off under vacuum and the residue is dissolved in absolute ethanol. The solution is evaporated to dryness. This procedure of dissolving in ethanol and driving off the solvent is repeated until a crystalline material is obtained. This is then recrystallized from methanol to provide a product, which melts at 183° C.

MS: m/z 266 ($C_{12}H_{14}N_2O_6$, $M^+$), 141 ($C_7H_9O_3$, sugar group), 126 ($C_5H_6N_2O_2$, base+H). The 1-(5-O-acetyl-2,3-dideoxy-β-D-glycero-pent-2-enofuranosyl)-thymine is dissolved in 25 mL of absolute pyridine and refluxed for 48 hours with 2 g of phosphorus pentasulfide. After cooling, the solution is decanted from the insolubles and evaporated to dryness under vacuum. The resulting residue is fractionated by column chromatography on Kieselgel 40 with chloroform as eluent. From the fractions containing the product, 265 mg of 1-(5-O-acetyl-2,3-dideoxy-β-D-glycero-pent-2-enofuranosyl)-4-thiothymine is obtained after recrystallization from methanol.

MS: m/z 282 ($C_{12}H_{14}N_2O_4S$, $M^+$, 141 ($C_7H_9O_3$, sugar group), 142 ($C_5H_6N_2OS$, base+H).

EXAMPLE 10

1-(2,3-Dideoxy-β-D-glycero-pent-2-enofuranosyl)-4-thiothymine

To 100 mg of the compound synthesized in Example 9, 10 mL of methanol are added, which had been saturated at 0° C. with ammonia. The reaction mixture is kept for 12 hours at room temperature and then evaporated to dryness. Crystals, melting at 117° C.–118° C., are obtained from methanol/ether.

MS: m/z 240 ($C_{10}H_{12}N_2O_3S$, M+), 209 ($C_9H_9N_2O_2S$, M-$H_2O$), 142 ($C_5H_8N_2OS$, base+H).

EXAMPLE 11

1-(2,3-Dideoxy-3-fluoro-β-D-ribofuranosyl)-4-thiothymine-5'-triphosphate 1-(2,3-Dideoxy-3-fluoro-β-D-ribofuranosyl)-4-thiothymine (60 mg, 0.21 mmoles) is dissolved in 0.5 mL of trimethyl phosphate and mixed at 0° C. with 0.0423 mL of phosphorus oxychloride (Yoshikawa et al., Tetrahedron Lett., 5065 (1967)). The reaction mixture is kept for 2 hours at 0° C., then treated with 10 mL of ice water and neutralized with triethylamine. After the addition of 300 mL of water, the reaction solution is fractionated column chromatographically on DEAE Sephadex chromatographic column with 0–0.3 moles/L of triethylammonium hydrogen carbonate as eluant. The 5'-monophosphate is isolated from the appropriate fractions. This product is converted by means of DOWEX WX 8 (pyridinium form) into the tri-n-butylammonium salt, activated after the removal of the solvent with N,N'-carbonyldiimidazole and converted with tetra-n-tributylammonium pyrophosphate in DMF by a known procedure (D. E. Huard et al., J. Am. Chem. Soc. 87, 1785 (1965)) into the 5'-triphosphate. The compound is eluted on DEAE Sephadex with a gradient of 0–0.5 moles/L of triethylammonium hydrogen carbonate. From the appropriate fractions, a product is obtained from which, after removal of the eluant, the sodium salt of the title compound is obtained by a known method with sodium iodide. The phosphate content is determined to be 16%.

The following Examples 12–15 and 17–20 are compounds represented by Formula (IV).

EXAMPLE 12

1-(2,3-dideoxy-3-fluoro-β-D-ribofuranosyl)-2-thiothymine 300 mg (1.3 mmol) of 2.5-anhydro-1-(2,3-dideoxy-3-fluoro-β-D-ribofuranosyl)-thymine are dissolved in 40 ml of dimethylformamide (DMF) and 3.5 ml of triethylamine. The mixture is cooled to –70° C., saturated with hydrogen sulfide and stored at room temperature for 5 days. The solvent is then removed under vacuum and the residue applied to a column containing 70 g of silica gel (50–70 mesh, MERCK). After removal of unidentified material with chloroform, the 1-(2,3-dideoxy-3-fluoro-β-D-ribofuranosyl)-2-thiothymine is eluted with chloroform (10% methanol) and crystallized from ethanol (234 mg, m.p. 173° C.–176° C.).

UV (methanol): max 220 nm (ε15900) and 277 nm (ε17300). MS:m/z 260 (M+, $C_{10}H_{13}N_2O_3S$ F).

EXAMPLE 13

1-(5-O-acetyl-2,3-dideoxy-3-fluoro-β-D-ribofuranosyl)-2-thiothymine 3 ml of acetic anhydride are added to a solution of 174 mg (0.67 mmol) of 1-(2,3-dideoxy-3-fluoro-β-D-ribofuranosyl)-2-thiothymine in 20 ml of dry pyridine. The mixture is stored at room temperature overnight. After evaporation of the solvent under reduced pressure, the residue is dissolved in chloroform and applied to a column containing 50 g of silica gel (50–70 mesh, MERCK). The 1-(5-O-acetyl-2,3-dideoxy-3-fluoro-β-D-ribofuranosyl)-2-thiothymine is eluted with chloroform and crystallized from methanol to produce a product having a m.p. of 171.5° C.–172.5° C.

UV (methanol): max 221 nm (ε15900) and 277 nm (ε17600). MS:m/z 302 (M+, $C_{12}H_{15}N_2O_4S$ F).

EXAMPLE 14

1-(5-O-acetyl-2,3-dideoxy-3-fluoro-β-D-ribofuranosyl)-2,4-dithiothymine

A mixture of 89 mg (0.29 mmol) of 1-(5-O-acetyl-2,3-dideoxy-3-fluoro-β-D-ribofuranosyl)-2-thiothymine and 500 mg of phosphorous pentasulfide in 15 ml of dry pyridine is heated under reflux for 5 hr. The cooled mixture is evaporated. The crude product is purified trough column chromatography on silica gel (50–70 mesh, MERCK) with chloroform as eluent to give 63 mg of the title compound. This material is recrystallized from toluene/n-hexane resulting in a product having a m.p. of 113° C.–114° C.

max (MeOH): 281.5 nm (ε22500) and 212 nm (ε5800). MS:m/z 318 (M+, $C_{12}H_{15}N_2O_3S_2F$).

EXAMPLE 15

1-(2,3-dideoxy-3-fluoro-β-D-ribofuranosyl)-2,4-dithiothymine 49 mg (0.15 mmol) of the acetylated compound are dissolved in 10 ml of methanol saturated with ammonia and maintained at room temperature for 16 hrs. The solvent is removed under vacuum and the resulting residue is purified by chromatography on a silica gel column using chloroform (1% methanol) to obtain 31 mg of the 1-(2,3-dideoxy-3-fluoro-β-D-ribofuranosyl)-2,4-dithiothymine as yellow crystals having a m.p. of 163.5° C.–165° C.

UV (MeOH): max 281 nm (ε23900) and 233 nm (ε1900). Anal.: calculated for $C_{10}H_{13}N_2O_2S_2F$: C 43.46; H 4.74; N 10.13; S 23.20. Found: C 43.37; H 4.72; N10.07; S 22.87.

EXAMPLE 16

1-(2,3-dideoxy-3-fluoro-β-D-ribofuranosyl)-5-ethyl-4-thiouracil 1-(5-O-acetyl-2,3-dideoxy-3-fluoro-β-D-ribofuranosyl)-5-ethyluracil (63 mg, 0.2 mmol) and phosphorous pentasulfide (500 mg) are suspended in 15 ml of dry pyridine and heated under reflux for 6 hrs. The cooled mixture is evaporated to dryness and the resulting residue is dissolved in 25 ml methanol saturated with ammonia and stored overnight. After evaporation of the solvent, the residue is applied to a column containing 100 g of silica gel (50–57 mesh, MERCK). Elution with chloroform (0.5% methanol) provides the title compound having a m.p. of 139°–140° C.

UV (MeOH): max 334 nm (ε19500). MS: m/z 274 (M+, $C_{11}H_{15}N_2O_3S$ F).

EXAMPLE 17

(±)-1-[1β,4β)-4-(trityloxymethyl)-cyclopent-2- en-1-yl]-2-thiothymine

A solution of (±)-1-[1β,3β,4β)-3-hydroxy-4-(trityloxymethyl)-cyclopentyl]-2-thiothymine (80 mg; 0.16 mmol) in 5 ml dry dichloromethane is treated with diethylamino sulfur trifluoride (DAST, 77 mg, 0.48 mmol). The solution is stirred for 1 hr and an additional amount of DAST (50 mg) is added. The reaction extracted with a saturated solution of NaH—$CO_3$ (5 ml). Column chromatography on silica gel (63–200 m. MERCK) with n-hexane as eluent to provide 12 mg of the unsaturated compound as a while solid material.

UV (methanol): max=275 nm (ε12700). MS: m/z 480 (M+, $C_{30}H_{28}N_2O_2S$).

EXAMPLE 18

(±)-1-[1β,3,4β)-3-fluoro-4-(trityloxymethyl)- cyclopentyl]-2-thiothymine

Further elution of the same column with chloroform/n-hexane (1/1; V/V) as eluent provides the title compound as the main produce as a light-yellow solid matter.

UV (methanol): max=273 273.5 nm (ε11900). MS: m/z 500 (M+, $C_{30}H_{29}O_2N_2S$ F).

EXAMPLE 19

(±)-1-[1β,4β2 )-4-(hydroxymethyl)-cyclopent-2-en-1-yl]-2- thiothymine 100 mg of the 4-trityloxymethyl compound obtained in accordance with Example 18 is dissolved in 5 ml of 80% acetic acid and heated under reflux for 10 minutes. The cold reaction mixture is evaporated to dryness and the residue is purified by column chromatography on silica gel (35–70 mesh; MERCK) with chloroform as eluent to provide the title compound as a single compound on tlc.

MS: m/z 238 (M+, $C_{11}H_{14}N_2O_2S$).

EXAMPLE 20

(±)-1-[1β,3α,4β)-3-fluoro-4-(hydroxymethyl)- cyclopentyl]-2-thiothymine

A solution of the 3α-fluoro-4β-trityloxymethyl (150 mg) obtained in accordance with Example 18 is heated under reflux for 2 hrs in 10 ml of acetic acid (80%). The solvent is evaporated under reduced pressure and the residue is fractionated by column chromatography on silica gel (35–70 mesh, MERCK) with chloroform (2% methanol) as eluent to provide 30 mg(±)-1-[1β,3α,4β)-3-fluoro-4-(hydroxymethyl)-cyclopentyl]-2-thiothymin MS: m/z 258 (M+, $C_{11}H_{15}N_2O_2S$ F).

We claim:

1. A substituted pyrimidine nucleoside selected from the group consisting of:

1-(2,3-dideoxy-3-fluoro-β-D-ribofuranosyl)-5-methyl-pyrimidine-2-one,
1-(2,3-dideoxy-3-fluoro-β-D-ribofuranosyl)-4-thiothymine,
1-(2,3-dideoxy-3-fluoro-β-D-ribofuranosyl)-4-hydroxylamino-5-methyl-(1H)-pyrimidine-2-one,
5-chloro-1-(2,3-dideoxy-3-fluoro-β-D-ribofuranosyl)-4-thiouracil,
1-(2,3-dideoxy-3-fluoro-β-D-ribofuranosyl)-(1H)-pyrimidine-2-one,
1-(2,3-dideoxy-3-fluoro-β-D-ribofuranosyl)-4-thiouracil,
1-(2,3-dideoxy-3-fluoro-β-D-ribofuranosyl)-4-hydroxylamino-(1H)-pyrimidine-2-one,
1-(2,3-dideoxy-β-D-glycero-pent-2-enofuranosyl)-4-thiothymine,
1-(2,3-dideoxy-βD-glycero-pent-2-enofuranosyl)-5-methyl-(1H)-pyrimidine-2-one,
1-(2,3-dideoxy-β-D-glycero-pent-2-enofuranosyl)-4-hydroxylamino-(1H)-pyrimidine-2-one,
1-(2,3-dideoxy-β-D-glycero-pent-2-enofuranosyl)-4-dimethylamino-(1H)-pyrimidine-2-one,
1-(2,3-dideoxy-3-fluoro-β-D-ribofuranosyl)-5-methyl-pyrimidine-2-one,
1-(2,3-dideoxy-3-fluoro-β-D-ribofuranosyl)-pyrimidine-2-one,
2',3'-dideoxy-2',3'-didehydro-4-thiothymidine,
1-(2,3-dideoxy-3-fluoro-β-D-ribofuranosyl)-2-thiothymine,
1-(5-O-acetyl-2,3-dideoxy-3-fluoro-β-D-ribofuranosyl)-2-thiothymine,
1-(5-O-acetyl-2,3-dideoxy-3-fluoro-β-D-ribofuranosyl)-2,4-dithiothymine,
1-(2,3-dideoxy-3-fluoro-β-D-ribofuranosyl)-2,4-dithiothymine,
1-(2,3-dideoxy-3-fluoro-β-D-ribofuranosyl)-5-ethyl-4-thiouracil,
(±)-1-[1β,3,4β)-3-fluoro-4-(trityloxymethyl)-cyclopentyl]-2-thiothymine,
(±)-1-[1β,3α,4β)-3-fluoro-4-(hydroxymethyl)-cyclopentyl]-2-thiothymine,
3'-deoxy-4-thiothymidine,
1-(5-O-acetyl-2,3-dideoxy-3-fluoro-β-D-ribofuranosyl)-4-thiothymine,
1-(5-O-acetyl-2,3-dideoxy-3-fluoro-β-D-glycero-ribofuranosyl)-4-hydroxylamino-(1H) pyrimidine-2-one,
1-(2,3-dideoxy-3-fluoro-β-D-glycero-ribofuranosyl)-4-hydroxylamino-(1H)-pyrimidine-2-one,
1-(5-O-acetyl-2,3-dideoxy-3-fluoro-β-D-ribofuranosyl)-4-hydroxylamino-5-methyl-(1 H)-pyrimidine-2-one,
1-(5-O-acetyl-2,3-dideoxy-β-D-glycero-pent-2-enofuranosyl)-4-thiothymine, and
1-(2,3-dideoxy-3-fluoro-β-D-ribofuranosyl)-4-thiothymine-5'-triphosphate.

\* \* \* \* \*